US009931099B1

(12) United States Patent
Fatteh et al.

(10) Patent No.: US 9,931,099 B1
(45) Date of Patent: Apr. 3, 2018

(54) ELECTRONIC STETHOSCOPE LACKING AN EARPIECE ASSEMBLY

(71) Applicants: Faiz Fatteh, Plantation, FL (US); Imtiaz Fatteh, Plantation, FL (US)

(72) Inventors: Faiz Fatteh, Plantation, FL (US); Imtiaz Fatteh, Plantation, FL (US)

(*) Notice: Subject to any disclaimer, the term of this patent is extended or adjusted under 35 U.S.C. 154(b) by 0 days.

(21) Appl. No.: 15/285,159

(22) Filed: Oct. 4, 2016

(51) Int. Cl.
| A61B 7/04 | (2006.01) |
| A61B 5/00 | (2006.01) |
| A61B 7/00 | (2006.01) |
| A61B 5/0205 | (2006.01) |

(52) U.S. Cl.
CPC .............. *A61B 7/04* (2013.01); *A61B 5/0004* (2013.01); *A61B 5/0024* (2013.01); *A61B 5/0205* (2013.01); *A61B 5/6823* (2013.01); *A61B 5/725* (2013.01); *A61B 5/7282* (2013.01); *A61B 5/742* (2013.01); *A61B 5/7405* (2013.01); *A61B 7/003* (2013.01); *A61B 2560/045* (2013.01); *A61B 2562/0204* (2013.01)

(58) Field of Classification Search
CPC ......... A61B 7/04; A61B 5/004; A61B 5/0024; A61B 5/0205
See application file for complete search history.

(56) References Cited

U.S. PATENT DOCUMENTS

| 2010/0145723 A1* | 6/2010 | Hudson | G06F 19/324 705/2 |
| 2014/0276229 A1* | 9/2014 | Ikeda | A61B 7/04 600/586 |
| 2016/0100817 A1* | 4/2016 | Hussain | A61B 7/04 600/301 |
| 2016/0287207 A1* | 10/2016 | Xue | A61B 7/04 |
| 2017/0128034 A1* | 5/2017 | Chong | A61B 7/04 |

* cited by examiner

*Primary Examiner* — Simon King
(74) *Attorney, Agent, or Firm* — Patents on Demand P.A.; Brian K. Buchheit

(57) ABSTRACT

An electronic stethoscope lacking an earpiece assembly can include a chestpiece base. The base can include a diaphragm, a transducer, a computer readable storage medium, and a transceiver. The transducer can detect analog auscultatory sounds from an auscultatory source and convert the sounds to a digital encoding. The encoding can be transmitted to a proximate or remote computing device via a secure communication channel. The earpiece assembly can be a cavity for transmitting the analog auscultatory sound from the base to the ear canal of a user.

20 Claims, 6 Drawing Sheets

ELECTRONIC STETHOSCOPE LACKING AN EARPIECE ASSEMBLY

BACKGROUND

The present invention relates to the field of electronic medical equipment and, more particularly, to an electronic stethoscope lacking an earpiece assembly.

Stethoscopes have long been an intrinsic aid in primary medical assessment of patient health. Stethoscopes provide valuable insight into the cardiopulmonary health of a patient and can be used by a trained professional to quickly diagnose medical conditions. In many instances, stethoscopes can be used to hear auscultatory sounds which can vary in intensity and clarity based on patient type and stethoscope user. Frequently when physicians consult with their peers to identify an irregularity in these sounds, each peer must listen to the auscultatory sounds independently and often may not hear the same sounds. This can often lead to disagreement between peers and uncertainty in an irregularity presence. Uncertainty can detract from the pursuit of providing the best medical care for patients and as such a better mechanism for sharing auscultatory sounds rapidly is needed.

BRIEF SUMMARY

One aspect of the present invention can include a method for an electronic stethoscope lacking an earpiece assembly. An electronic stethoscope lacking an earpiece assembly can include a chestpiece base. The base can include a diaphragm, a transducer, a computer readable storage medium, and a transceiver. The transducer can detect analog auscultatory sounds from an auscultatory source and convert the sounds to a digital encoding. The encoding can be transmitted to a proximate or remote computing device via a secure communication channel. The earpiece assembly can be a cavity for transmitting the analog auscultatory sound from the base to the ear canal of a user.

Another aspect of the present invention can include a system for an electronic stethoscope lacking an earpiece assembly. An electronic stethoscope lacking an earpiece assembly can include a chestpiece base. The base can include a diaphragm, a transducer, a computer readable storage medium, and a transceiver. The transducer can detect analog auscultatory sounds from an auscultatory source and convert the sounds to a digital encoding. The encoding can be transmitted to a proximate or remote computing device via a secure communication channel. The earpiece assembly can be a cavity for transmitting the analog auscultatory sound from the base to the ear canal of a user. A companion application configured to communicate with the electronic stethoscope.

Yet another aspect of the present invention can include a computer program product that includes a computer readable storage medium having embedded computer usable program code. The computer usable program code can be configured to communicate with an electronic stethoscope. The electronic stethoscope can lack an earpiece assembly. The stethoscope can include a chestpiece base, a transducer, a computer readable storage medium, and a transceiver. The transducer can detect analog auscultatory sounds from a physiology of a user and converts the sounds to a digital encoding. The encoding can be wirelessly transmitted to a proximate or remote computing device via the application. The earpiece assembly can be a cavity for transmitting the analog auscultatory sound from the base to the ear canal of a user.

DETAILED DESCRIPTION

Figure 1A:
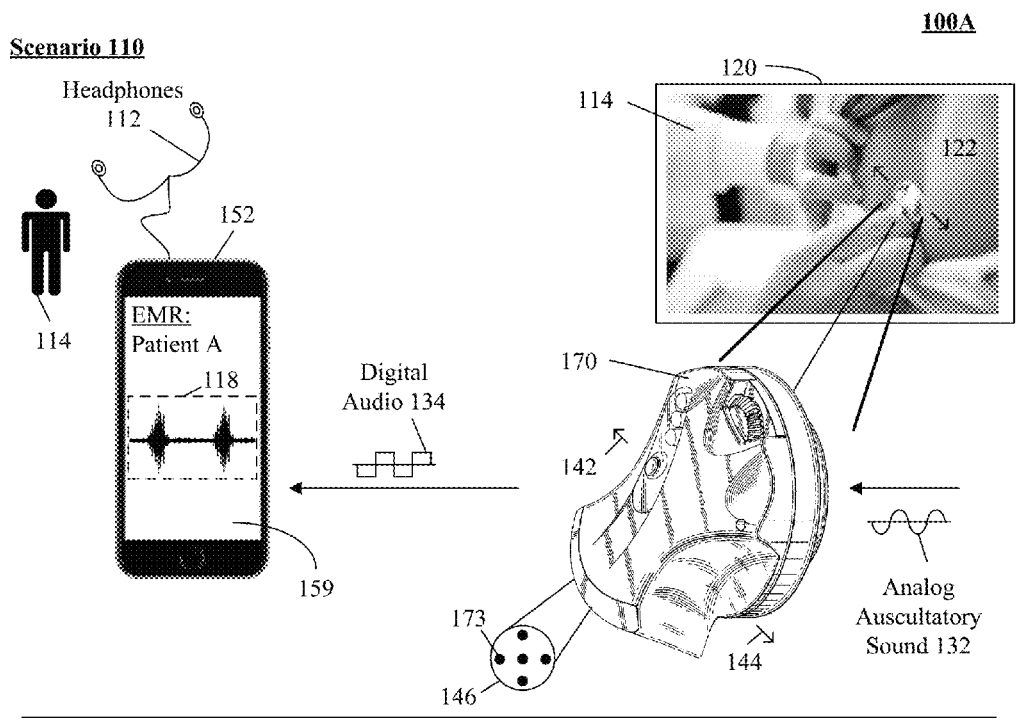
FIG. 1A is a schematic diagram illustrating a scenario and a system for an electronic stethoscope lacking an earpiece assembly in accordance with an embodiment of the inventive arrangements disclosed herein.
Figure 1A:
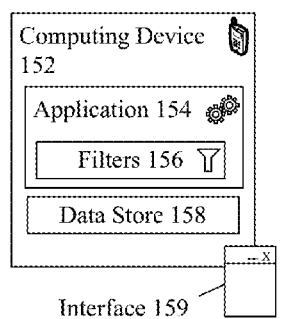
Figure 1A:
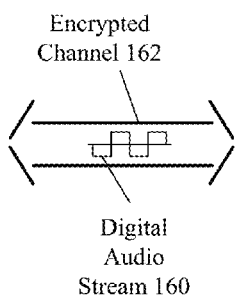
Figure 1A:
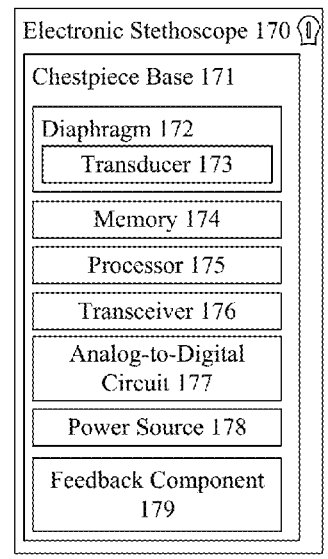

The present disclosure is a solution for an electronic stethoscope lacking an earpiece. In the solution, electronic stethoscope can include an electroacoustic transducer, a computer readable storage medium, and a wireless transmitter. In one instance, the stethoscope can include a headphone audio output port which can permit the user of electronic headphones to be connected to the stethoscope. In the instance, auscultatory sounds captured by the transducer can be presented within the headphones in real-time or near real-time. In one embodiment, the stethoscope can wirelessly convey analog auscultatory sounds which have been digitally encoded to a communicatively linked computing device. In the embodiment, the computing device can visually and/or aurally present the digitally encoded auscultatory sounds within a display or audio output component.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIG. 1A is a schematic diagram illustrating a scenario 110 and a system 150 for an electronic stethoscope lacking an earpiece assembly in accordance with an embodiment of the inventive arrangements disclosed herein. Scenario 110 and system 150 can be present in the context of interfaces 210, 220, 230, system 250, method 300, diagram 410, and/or embodiments 510, 530, 550. It should be appreciated that scenario 110 can be performed in the context of system 150. In scenario 110, a binaural electronic stethoscope utilized by a physician 114 (e.g., user) can capture analog auscultatory sound 132 from patient 122 during auscultation 120. In the scenario, sound 132 can be converted into a digital audio 134 which can be wirelessly transmitted to mobile phone 152 (e.g., via BLUETOOTH). The mobile phone 152 can present a visual (e.g., phonocardiogram 118 in interface 159) or audio (e.g., playback on headphones 112) presentation of the audio 134. That is, the stethoscope can permit visualization and/or playback of heart and lung sounds (e.g., S1/S2's), murmurs, bruits, and the like.

As used herein, an electronic stethoscope 170 can be a device for auscultation. Stethoscope 170 can include a chestpiece base 171 but lack an earpiece assembly. Chestpiece base 171 can include a diaphragm 172, memory 174, process 175, transceiver 176, analog-to-digital circuit 177, power source 178, feedback component 179, user input components (e.g., switches), a display (not shown), and the like. Stethoscope 170 can include or lack an analog output port, a digital out port (e.g., USB, optical out), a charging port, and the like.

It should be appreciated that stethoscope can overcome the low sound levels by electronically amplifying body sounds (e.g., heart, lungs, bowels). However, amplification of stethoscope contact artifacts and component cutoffs (e.g., frequency response thresholds of electronic stethoscope microphones, pre-amps, amps, and speakers) limit electronically amplified stethoscopes' overall utility by amplifying mid-range sounds, while simultaneously attenuating high- and low-frequency range sounds. This limitation can be overcome through the use of different technologies for sampling sound, digital signal processing, filtering, and the like.

As used herein, an analog auscultatory sound 132 can be a continuous audio signal which varies continuously with the pressure of the sound waves. A digital audio 134 can be a signal in which the continuous quantity of sound 132 can be represented by a sequence of discrete values which take on one of a finite number of values. As used herein, headphones 112 can be an analog output device able to playback digital audio 134 or analog sound 132.

In scenario 110, user 114 can utilize electronic stethoscope 170 to capture analog auscultatory sounds 132. In one instance, sound 132 can be digitally encoded in real-time or near real-time. In the instance, sound 132 can be conveyed to wirelessly connected mobile phone 152. Interface 159 can present phonocardiogram in real-time or near real-time permitting user 114 to perform manual and/or automatic analysis of the sound 132 (as audio 134). In one embodiment, interface 159 can permit the addition of audio 134 to an electronic medical record of a patient (e.g., Patient A). In the embodiment, audio 134 can be directly compared to historic recordings.

It should be appreciated that the stethoscope 170 can record sound 132 in a "raw" format such as an audio bitstream (e.g., Waveform Audio File Format). In one instance, the audio 134 can be encoded in a perceptual audio encoding such as MPEG-2 Audio Layer III (MP3), OGG, and the like. It should be appreciated that the audio 134 can be stored in any arbitrary lossless format including, but not limited to, Free Lossless Audio Codec (FLAC), MPEG-4 Scalable to Lossless (MPEG-4 SLS), and the like. In one instance, sound 132 can be converted within hardware/software of stethoscope to audio 134.

In one instance, a training mode can be activated permitting user guidance in positioning of stethoscope 170. In the training mode, one or more feedback components 179 can direct the user 114 to adjust the position of stethoscope on patient 122 to improve sound 132 quality (e.g., amplitude). For example, training mode can be employed to teach medical students approximate correct positions (e.g., learning triangle of auscultation) for placing stethoscope. In one instance, a directional vibration can be utilized to indicate a direction which stethoscope can be adjusted. In the instance, directional vibration can correspond to cardinal directions (e.g., up, down, left, right) but is not limited in this regard. In another instance, a display on stethoscope can be used to visually indicate a direction in which the stethoscope can be repositioned. For example, a green arrow pointing toward the left can indicate the user can shift the stethoscope left to improve sound 132 capture.

In system 150, computing device 152 can execute an application 154 which can receive digital audio stream 160 via encrypted channel 162. In one embodiment, application 152 can include one or more filters 156 (e.g., low passband) which can be applied to stream 160 during one or more manual and/or automated analysis. In the embodiment, application 154 can be a mobile application, a Web-based service executing within a Web browser, and the like. Device 152 can include data store 158, interface 159, and the like. Data store 158 can store application 154 settings, filters 156, digital audio stream 160, and the like.

It should be appreciated that channel 162 can be a non-encrypted channel. In one instance, stream 160 can be encrypted, compressed, and the like. In the instance, stream 160 can be encrypted utilizing traditional and/or proprietary encryption technologies. For example, encryption of stream 160 can utilize public/private key encryption.

In one instance, memory 174 can include volatile memory, non-volatile memory, and the like. In one instance, transceiver 176 can be a Bluetooth Low Energy (BLE) transceiver. In the instance, the transceiver 176 can include a transmitter.

It should be appreciated that stethoscope 170 can be communicatively linked via one or more wired or wireless communication channels including, but not limited to, Ethernet, WiFi, near field communication, and the like. In the system 150, stethoscope 170 can be communicatively linked via a BLUETOOTH communication protocol. Protocol can include, Synchronous Connection-Oriented (SCO), Asynchronous Connection-Less (ACL), and the like. For example, the stethoscope can permit the use of BLUETOOTH Hearing-Aid Compatible, a BLUETOOTH headset, BLUETOOTH headphones, and the like.

Electronic stethoscope 170 can require conversion of acoustic sound waves to electrical signals which can then be amplified and processed for optimal listening. It should be appreciated that transducer 173 can include any traditional and/or proprietary technology and can be supplanted by technology with superior capabilities. For example, stethoscope 170 can include a piezoelectric crystal at the head of a metal shaft where the bottom of the shaft making contact with a diaphragm, a piezo-electric crystal placed within foam behind a thick rubber-like diaphragm (e.g., diaphragm 172) or an electromagnetic diaphragm with a conductive inner surface to form a capacitive sensor (e.g., diaphragm 172 responds to sound waves, with changes in an electric field replacing changes in air pressure). It should be appreciated that stethoscope can include a digital signal processor (DSP), video processing unit (VPU), and the like. In one instance, stethoscope 170 can leverage device 152 components including, display, DSP, VPU, and the like.

In one instance, stethoscope 170 can utilize both an electroacoustic transducer and a piezoelectric transducer (e.g., transducer 173). In the instance, sound 132 capture from each transducer can be independently selected and/or combined to produce a high fidelity audio 134 of sounds 132. In one embodiment, application 154 can permit the selection or combination of audio 134 for manual and/or automated analysis.

In one embodiment, stethoscope 170 can include an array 146 of transducers 173 arranged in a geometric pattern (e.g., cross, circle, grid). In the embodiment, transducers 173 can be utilized to increase the fidelity of sound 132 captured through audio interpolation, audio proximity, and the like. In one instance, process 175 and/or application can perform digital signal processing on sound 132 and/or audio 134 to produce a high resolution recording (e.g., sampling rates higher than 44100 Hz, pulse density modulation). In one configuration, each transducer of array 146 can individually sample sound 132 and can be encoded into an audio track. In the configuration, each audio track can be compiled into an aggregate audio 134 file where each track can be played individually or together.

Stethoscope 170 can include a functionality which enables switching between analog and digital playback, recording, and the like. In one instance, stethoscope 170 can permit live streaming of stream 160 via one or more encrypted channels 162. In one configuration of the instance, stethoscope 170 and/or application 154 can permit multi point streaming permitting multiple devices to receive audio 134 in real-time or near real-time. It should be appreciated that the configuration can be assisted via one or more servers and/or software programs.

As used herein, an analog-to-digital circuit 177 can be an electronic circuit able to convert analog signal into a digital signal. That is, circuit 177 can convert an input analog voltage or current to a digital number proportional to the magnitude of the voltage or current. In one instance, circuit 177 can convert analog sound 132 to digital audio 134 utilizing traditional and/or proprietary architectures.

As used herein, a phonocardiogram 118 (PCG) can be a plot of high-fidelity recording of the sounds and murmurs made by the heart. PCG 118 can include a video sample over time such as a Real-Time Phonocardiogram Visualization. PCG 118 can include sounds from vibrations created by closure of the heart valves, respiration, and the like. Vibrations from the heart can include, but not limited to, atrioventricular valves closure aortic valve and pulmonary valve closure, and the like.

As used herein, an electronic medical record can be a systematized collection of patient and population electronically-stored health information in a digital format. The record can include a range of data, including, but not limited to, phonocardiogram, demographics, medical history, medication and allergies, immunization status, laboratory test results, radiology images, vital signs, personal statistics like age and weight, billing information, and the like. It should be appreciated that records can be shared across different health care providers (e.g., servers can be communicatively linked). It should be understood that electronic medical record can include electronic health records, an auscultation reports (e.g., Portable Document Format), and the like.

In one embodiment, stethoscope 170 can be a consumer device enabling average users to perform at-home auscultation. In the embodiment, stethoscope 170 can show basic assessment and can convey results to a primary care establishment (e.g., physician). That is, audio 134 can be included in an automated email to a user's primary care physician when stethoscope is used at-home.

Drawings presented herein are for illustrative purposes only and should not be construed to limit the invention in any regard. In one embodiment, channel 162 can lack encryption. In one instance, system 150 can be a functionality of an application programming interface. It should be appreciated that stethoscope 170 shape and/or size can conform to traditional geometries. In one instance, stethoscope 170 can include an ergonomic chestpiece base 171 which can fit comfortably when in use by user 114.

It should be appreciated that one or more components within system 150 can be optional components permitting that the disclosure functionality be retained. It should be understood that system 150 components can be optional components providing that stethoscope 170 functionality is maintained. It should be appreciated that one or more components of stethoscope 170 can be combined and/or separated based on functionality, usage, and the like. System 150 can conform to a Service Oriented Architecture (SOA), Representational State Transfer (REST) architecture, and the like. In one embodiment, application 154 can be a functionality of a Web-based Service, an Asynchronous Javascript and Extensible Markup Language (AJAX) functionality, Web application, and the like.

Data store 158 can be a hardware/software component able to persist application settings, filters 156, audio stream 160, and the like. Data store 158 can be a Storage Area Network (SAN), Network Attached Storage (NAS), and the like. Data store 158 can conform to a relational database management system (RDBMS), object oriented database management system (OODBMS), and the like. Data store 158 can be communicatively linked to a server in one or more traditional and/or proprietary mechanisms. In one instance, data store 158 can be a component of Structured Query Language (SQL) complaint database. In one embodiment, data store 158 can be a removable storage media including, but not limited to, a Secure Digital (SD) card, a Secure Digital High Capacity (SDHC) card, a Compact Flash (CF) card, and the like.

As used herein, a transceiver 176 can be a component able to transmit and receive information to and from device 152 and/or stethoscope 170. Transceiver 176 can communicatively link device 152 and/or stethoscope 170 to one or more networks, where the communication link can be a wired or wireless link.

A network can be an electrical and/or computer network connecting one or more system 150 components. Network can include, but is not limited to, twisted pair cabling, optical fiber, coaxial cable, and the like. Network can include any combination of wired and/or wireless components. Network topologies can include, but is not limited to, bus, star, mesh, and the like. Network types can include, but is not limited to, Local Area Network (LAN), Wide Area Network (WAN), Virtual Private Network (VPN) and the like.

Figure 1B:
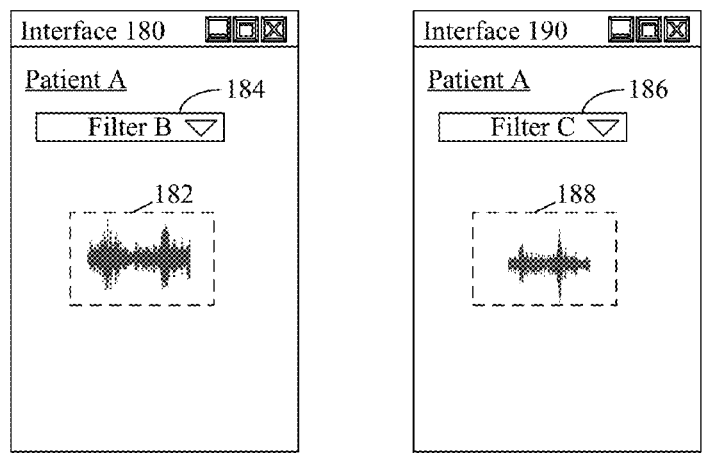
FIG. 1B is a schematic diagram illustrating a set of interfaces for an electronic stethoscope lacking an earpiece assembly in accordance with an embodiment of the inventive arrangements disclosed herein.

FIG. 1B is a schematic diagram illustrating a set of interfaces 180, 190 for an electronic stethoscope lacking an earpiece assembly in accordance with an embodiment of the inventive arrangements disclosed herein. Interfaces 180, 190 can be present in the context of scenario 110, system 150, interfaces 210, 220, 230, system 250, method 300, diagram 410, and/or embodiments 510, 530, 550. In interfaces 180, 190, one or more filters can be applied to a digital audio 134 to isolate sounds of interest within audio 134. In the instances, filters 184, 186 can be utilized to present one or more portions of interest of audio 134. Filters 184, 186 can include, but are not limited to, masking filters (e.g., AND/OR), frequency filters (e.g. high bandpass), and the like. In one instance, filters can include presets (e.g., murmur) such as frequency ranges known for including irregularities. In interface 180, filter 184 can produce audio segment 182 which can be played back when filter 184 is applied. In interface 190, filter 186 can produce audio segment 188 which can be presented when filter 186 is applied.

Figure 2:
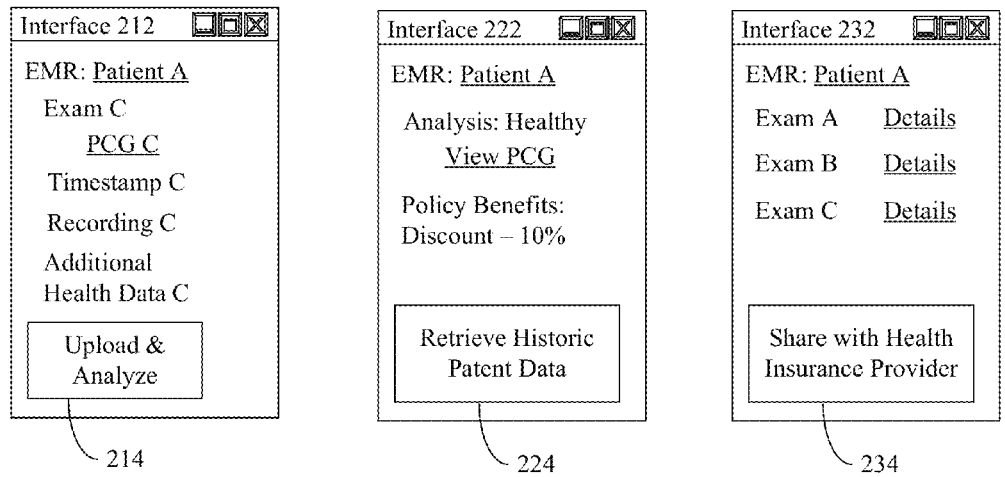
FIG. 2 is a schematic diagram illustrating a set of interfaces and a system for an electronic stethoscope lacking an earpiece assembly in accordance with an embodiment of the inventive arrangements disclosed herein.
Figure 2:
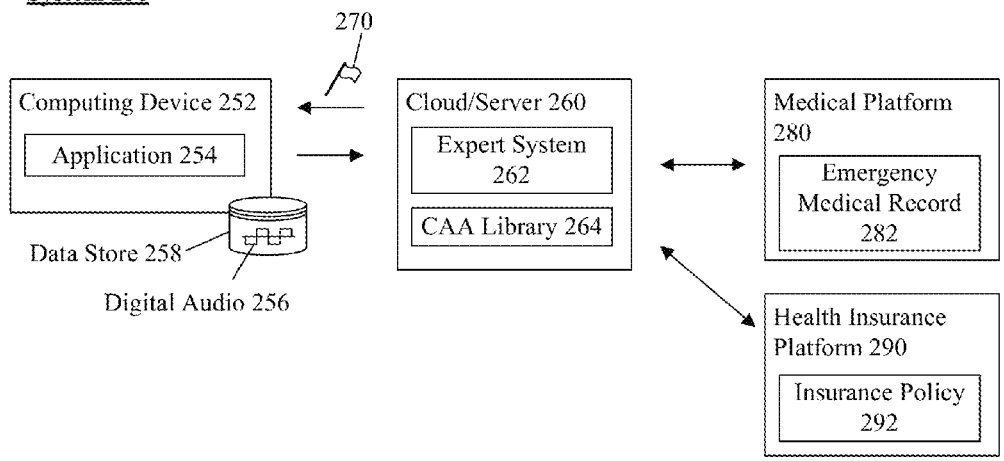

FIG. 2 is a schematic diagram illustrating a set of interfaces and a system for an electronic stethoscope lacking an earpiece assembly in accordance with an embodiment of the inventive arrangements disclosed herein. Interfaces 210, 220, 230 can be present in the context of scenario 110, system 150, interfaces 180, 190, system 250, method 300, diagram 410, and/or embodiments 510, 530, 550. In interface 212, an electronic stethoscope output can be directly linked to an electronic medical record. In one instance, interface 212-232 can be linked to computer-aided auscultation, HIPAA compliant services, and the like. Interfaces 212-232 can be performed in the context of system 250.

As used here, computer-aided auscultation (CAA) can be a clinical decision support system designed to assist physicians and other health professionals with decision making tasks when assessing a heart murmur. Computer-aided auscultation clinical decision support can leverage electronic stethoscope (e.g., 170) to record the acoustic heart sound. Computer analysis by one or more expert systems 262 can identify specific heart sounds that may be present, including S1, S2 and suspected murmurs. CAA can be linked to a graphical display with one or more visualizations of heart sounds, lung sounds, and the like.

In interface 212, an electronic medical record 282 of a patient can be presented. Interface 212 can permit a primary care personnel to convey a phonocardiogram and/or related patient data to an expert system 262 for analysis. For example, interface 212 can present a user interactive button 214 which can permit the immediate communication of a phonocardiogram to an expert system to retrieve an instant analysis report of patient health.

In interface 222, an analysis report 270 of a phonocardiogram obtained from electronic stethoscope 170 can be presented. In one instance, report can include broad assessment of patient health, specific details (e.g., murmur detected, absent, etc.), and the like. In one embodiment, a communicatively linked health insurance platform can be leveraged to present a health insurance policy benefit based on health assessment. For example, when a patient is determined to be healthy, a discount for subsequent medical services can be presented and/or redeemable. It should be appreciated that policy 292 information for patient can be obtained manually and/or automatically (e.g., via EMR data). In one instance, historic patient data can be retrieved and/or presented within interface 222 responsive to user interface element 224. Responsive to selection of element 224, interface 232 can be presented.

In interface 232, one or more electronic medical record details for a patient can be presented. In one instance, user interface element 234 can permit sharing of EMR with one or more insurance providers, medical institutes, and the like. In one embodiment, sharing EMR can include comparing patient PCG with a shared institutional library of sounds enabling analysis against a large data set. It should be appreciated that sharing can include the use of non-personally identifiable (e.g., sanitized) data sets which protect patient identity.

In system 250, a computing device 252 can execute an application 254 which can be communicatively linked with electronic stethoscope 170. In one instance, application 254 can leverage an application programming interface to perform the functionality described herein. In one embodiment, the application 254 can interface with electronic stethoscopes currently available on the commercial market. In the embodiment, application 254 can convert analog auscultatory sounds captured by an electronic stethoscope to a digital encoding. In the embodiment, data store 258 can persist digital audio 256 captured by electronic stethoscope 170 and/or different electronic stethoscopes.

Cloud/server 260 can be a hardware/software entity for executing an expert system 262. Expert system 262 can be a computer system that can emulate the decision-making ability of a human expert. In one instance, expert system 262 can perform CAA to automatically share audio 256 with medical platform 280 and/or platform 290. In the instance, system 262 can leverage CAA library 264 to determine severe or benign irregularities and perform automated actions accordingly.

In one instance, system 250 can trigger automatic insurance referrals to specialists care providers responsive to an analysis of audio 256 obtained from data store 258. In the instance, manual approval of referrals can be required to ensure reduced overhead for administrative staff while providing human centered approach to patient care.

Figure 3:
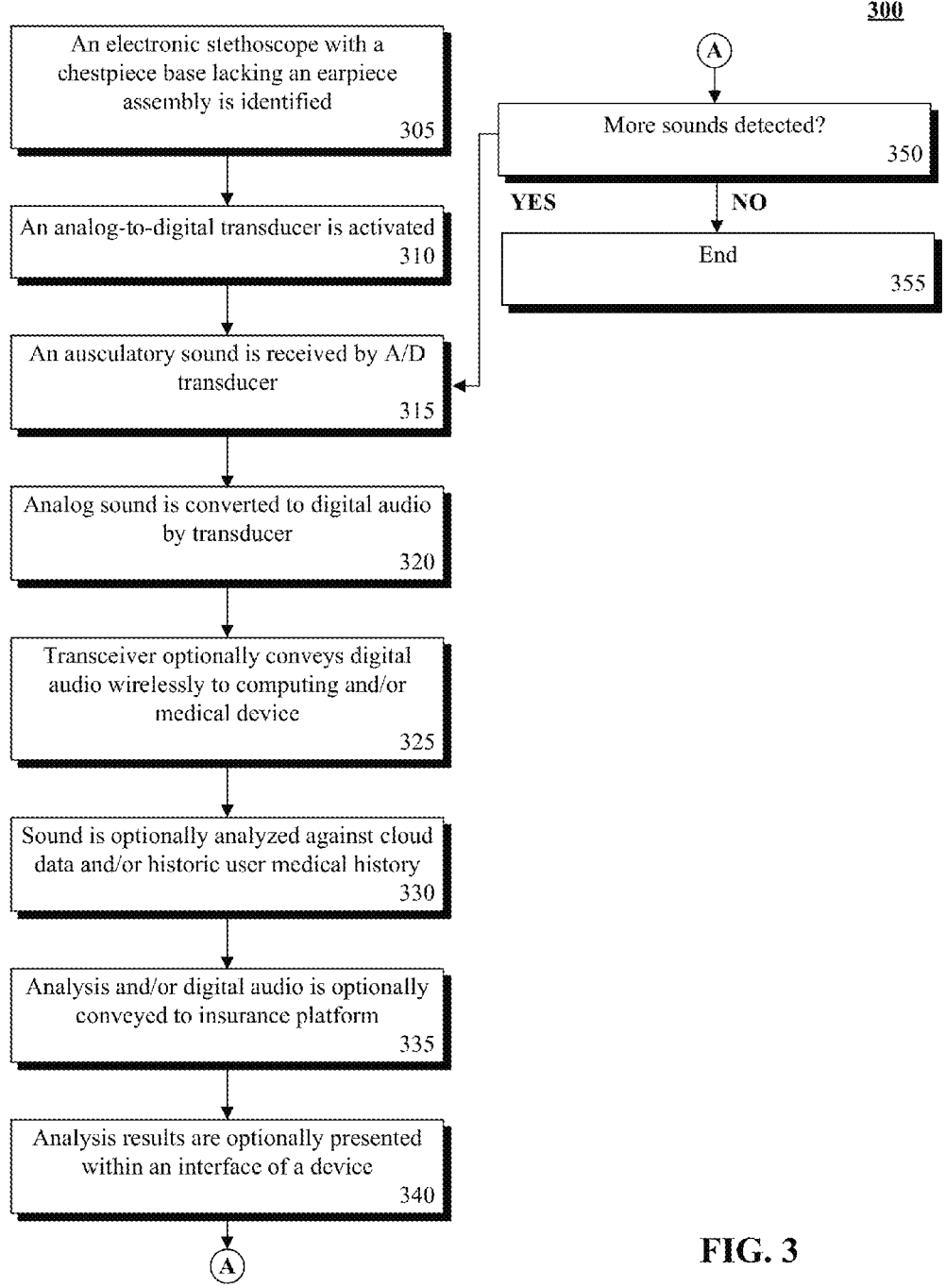
FIG. 3 is a schematic diagram illustrating a method for an electronic stethoscope lacking an earpiece assembly in accordance with an embodiment of the inventive arrangements disclosed herein.

FIG. 3 is a schematic diagram illustrating a method for an electronic stethoscope lacking an earpiece assembly in accordance with an embodiment of the inventive arrangements disclosed herein. Method 300 can be present in the context of scenario 110, system 150, interfaces 210, 220, 230, system 250, diagram 410, and/or embodiments 510, 530, 550. Method 300 can be performed in real-time or near real-time. Method 300 can be performed in serial and/or in parallel. In method 300, an electronic stethoscope lacking an earpiece assembly can convey a digitally encoded auscultatory sound to a communicatively linked device. The device can playback and/or present the digitally encoded auscultatory sound.

In step 305, an electronic stethoscope with a chestpiece base lacking an earpiece assembly can be identified. In step 310, an analog-to-digital transducer can be activated. In step 315, an auscultatory sound can be received by the analog-to-digital transducer. In step 320, the analog sound can be converted to digital audio by the transducer. In step 325, a transceiver can optionally convey the digital audio wirelessly to a computing and/or medical device. In step 330, the sound can be optionally analyzed against cloud data and/or historic user medical history. In step 335, the analysis and/or digital audio can be optionally conveyed to an insurance platform. In step 340, the analysis results can be optionally presented within an interface of a communicatively linked computing device. In step 350, if more sounds are detected, the method can return to step 315, else continue to step 355.

Figure 4:
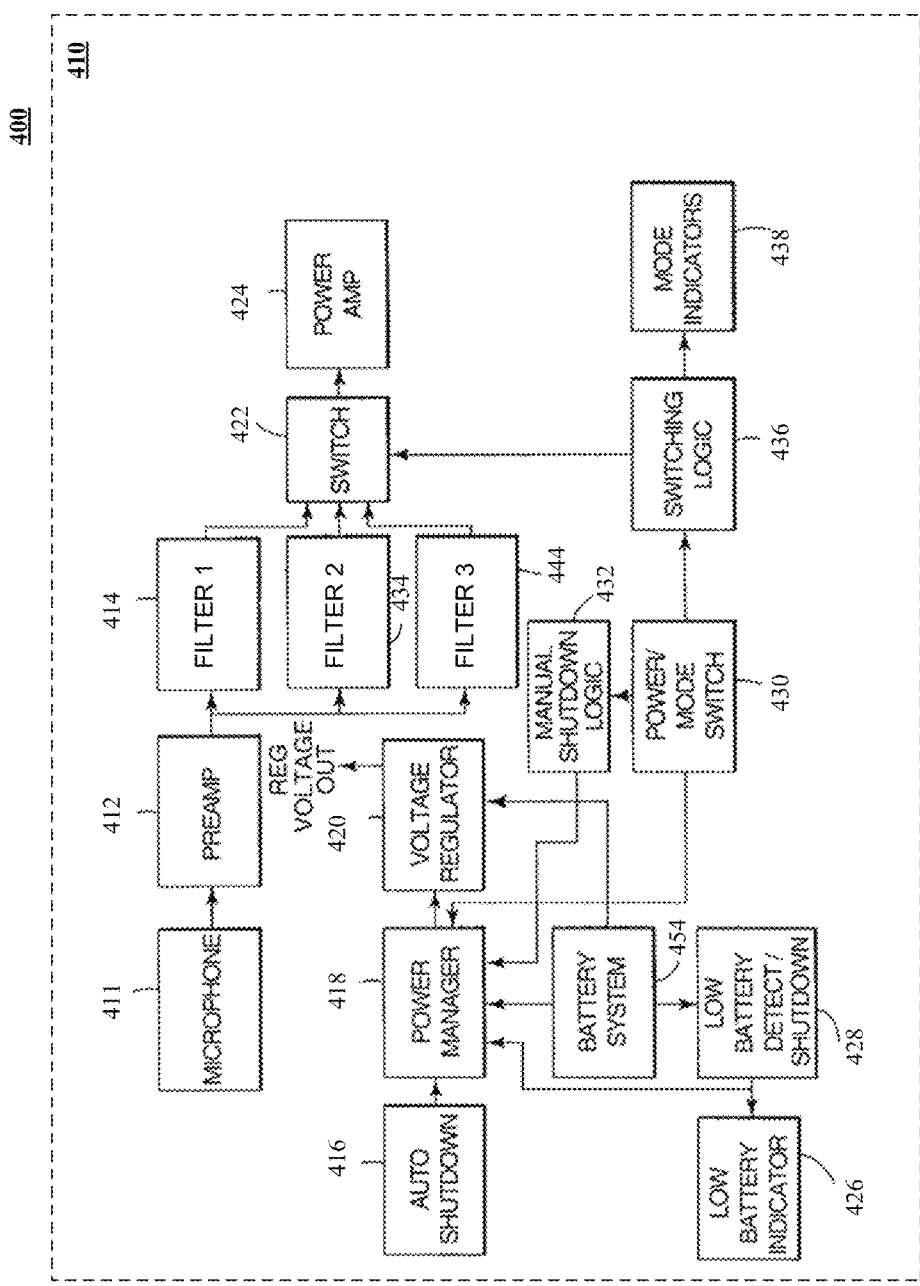
FIG. 4 is a schematic diagram illustrating an embodiment for a simplified block diagram of an electronic stethoscope lacking an earpiece assembly in accordance with an embodiment of the inventive arrangements disclosed herein.

FIG. 4 is a schematic diagram illustrating an embodiment for a simplified block diagram of an electronic stethoscope lacking an earpiece assembly in accordance with an embodiment of the inventive arrangements disclosed herein. Diagram 410 can be present in the context of scenario 110, system 150, interfaces 210, 220, 230, system 250, method 300, and/or embodiments 510, 530, 550.

In diagram 410, the sound capturing system of electronic stethoscope can be electronic. A simplified block diagram of the electronic sound capture system 410 can be illustrated with components 411-444. It should be appreciated that components 411-444 can include optional components. The sound capture system can include at least one microphone which can act as an acoustical transducer to receive auscultatory sounds from the body and transform the auscultatory sounds into an electrical signal. In an alternate embodiment, the stethoscope could include two or more microphones, although the system can be described with one microphone for purposes of illustration. This electrical signal can be amplified and filtered by preamp/high pass filter (e.g., 152). The preferred embodiment of the present electronic stethoscope can be designed to emulate the frequency response of a standard acoustical stethoscope in both bell and diaphragm modes, while providing additional features attainable only with an electronic stethoscope, such as signal amplification, noise reduction, wider bandwidth, and mode selection. In one embodiment, the stethoscope can include three or more major filters, 414, 434, 444, permitting the selection between three or more different "modes" of operation of the electronic stethoscope. That is, additional filters and/or modes could be added without departing from the scope of the present invention. Emulation of the frequency response of a standard acoustical stethoscope can be achieved with filters 434, 444. Filter 434 can emulate the diaphragm mode of a standard acoustical stethoscope, while filter 444 can emulate the bell mode of a standard acoustical stethoscope. Filter 414 can provide a wideband frequency response which allows a user to hear a broad range of frequencies, including high frequency sounds such as those produced by mechanical heart valves and the like. It should be appreciated that these sounds can occur in a frequency range that is not audible with most acoustic stethoscopes.

Power/mode switch 430 can provide for both power on of the circuitry and for mode selection in a single switch. Mode indicators 438 can provide visual or tactile indication to the user as to the current operational mode of the stethoscope. Switching logic 436 can be connected to power/mode switch 430 and can control electronic switch 422 which can determine which filter can be applied to form the output (e.g., digital encoding). Power amplifier 424 can receive the filtered signal and the signal can be output to an appropriate form (e.g., file or stream).

The stethoscope can be powered by a battery system 454, which can include commonly available disposable AAA batteries, a rechargeable Lithium Ion battery (e.g., convention, proprietary), and the like. A low battery detection/shutdown circuit 428 can monitor available battery power and can indicate when the battery power is running low via low battery indicator 426. When the voltage on the battery is below a predetermined level (e.g., 1 volt) the low battery detection/shutdown circuit 428 can remove power from the stethoscope.

To prolong battery system life, an automatic shutdown circuit 416 can automatically remove power from the stethoscope after it has not been used for a preselected period of time. In one embodiment, the automatic shutdown circuit can remove power a preselected period of time after the stethoscope is powered on. Alternatively, the automatic shutdown circuit can removes power a preselected period of time after the last time the mode changed. A voltage regulator 420 provides DC-DC conversion from the battery voltage to a higher voltage (e.g., 3.0 volts) and can regulate and filter the voltage provided to the stethoscope circuitry.

Figure 5:
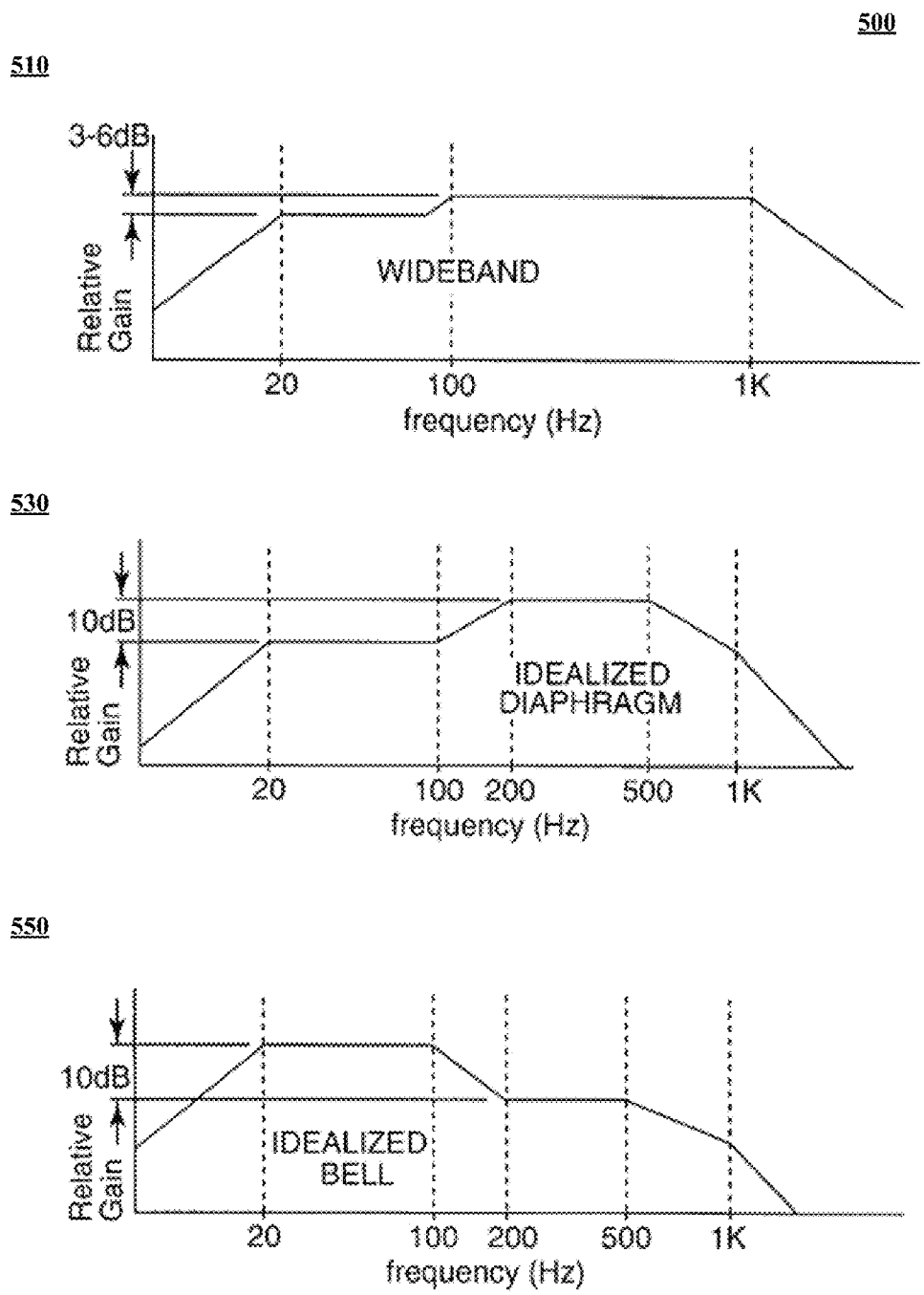
FIG. 5 is a schematic diagram illustrating a set of embodiments for frequency responses of the in the wideband, diaphragm, and bell modes of an electronic stethoscope lacking an earpiece assembly in accordance with an embodiment of the inventive arrangements disclosed herein.

FIG. 5 is a schematic diagram illustrating a set of embodiments 510, 530, 550 for frequency responses of the in the wideband, diaphragm, and bell modes of an electronic stethoscope lacking an earpiece assembly in accordance with an embodiment of the inventive arrangements disclosed herein. Embodiments 510, 530, 550 can be present in the context of scenario 110, system 150, interfaces 210, 220, 230, system 250, method 300, and/or diagram 410. The set of embodiments 510, 530, 550 can include exemplary filters (e.g., 156) which can correspond to different audio profiles or audio modes. Embodiment 510, 530 can represent an idealized diaphragm mode and an idealized bell mode. Embodiment 550 can represent a wideband mode.

The frequency response of an idealized bell filter can be shown in embodiment 550. The frequency response of an idealized diaphragm filter and is shown in embodiment 530. As shown in embodiments 530, 550 and as described in more detail below, the frequency responses of the filters are preferably spectrally separate. The frequency response of filter is shown in 510 and can provide a wideband frequency response. The wideband mode can pass body sounds and other high frequency sounds within a wide spectral band.

The idealized bell and diaphragm modes can cover the ranges of frequencies of the biological sounds of interest. The frequency content of the cardiac, respiratory, fetal, Korotkoffs sounds, and other biological sounds of interest can be present in an overall frequency range of about 20-2000 Hz. To allow the user to more easily hear and distinguish between sounds of interest of different frequencies, the idealized bell and diaphragm modes can each emphasize a different portion of this overall frequency range.

In the embodiment, the idealized diaphragm and idealized bell modes can each have an overall passband which can include an emphasized passband and a de-emphasized passband. For the idealized diaphragm mode, the emphasized passband can be in the range of about 200-500 Hz, while the de-emphasized passband can be in the range of about 20-200 Hz. For the idealized bell mode, the emphasized passband can be in the range of about 20-100 Hz, while the de-emphasized passband can be in the range about of 100-500 Hz. To provide the distinction between the emphasized and de-emphasized passbands, the relative amplitude of the emphasized passband can be greater than that of the de-emphasized passband.

The idealized diaphragm mode can emphasize the high-frequency sounds while preserving some of the low-frequency sounds. In this way, the idealized diaphragm mode can minimize masking of high-frequency sounds (e.g., cardiac murmurs) by low-frequency sounds. As shown in embodiment 530, the frequencies in the range of about 200-500 Hz can be emphasized and the frequencies in the range of about 20-200 Hz can be preserved but reduced in amplitude. To emphasize the frequencies in the range of about 200-500 Hz in the idealized diaphragm mode, the relative amplitude of the emphasized passband can be sufficiently greater than that of the de-emphasized passband such that the resulting difference is perceptible to a user, and the attenuation of the de-emphasized passband can be small enough such that the user can still hear the de-emphasized frequencies. For this purpose, a relative amplitude of the emphasized passband can be in the range of about 5-15 dB greater than the de-emphasized passband is appropriate, with a relative amplitude of about 10 dB.

Conversely, the idealized bell mode can emphasize the low-frequency sounds while preserving some of the high-frequency sounds. In this way, the idealized bell mode supports medical auscultation needs by minimizing psychoacoustic "masking" of low-frequency sounds by other sounds present at higher frequencies. As shown in embodiment 550, the frequencies in the range of about 20-100 Hz can be emphasized, while the frequencies in the range of about 100-500 Hz can be preserved but reduced in amplitude. To emphasize the frequencies in the range of about 20-100 Hz in the idealized bell mode, the relative amplitude of the emphasized passband can be sufficiently greater than that of the de-emphasized passband such that the resulting difference can be perceptible to a user, and the attenuation of the de-emphasized passband can be small enough such that the user can still hear the de-emphasized frequencies. For this purpose, a relative amplitude of the emphasized passband can be in the range of about 5-15 dB greater than the de-emphasized passband is appropriate, with a relative amplitude of about 10 dB.

In both the idealized bell and idealized diaphragm modes, attenuation in the range of about 500-1000 Hz can be about 12 dB/octave, and can be about 18 dB/octave above 1000 Hz. Because the human ear can be more sensitive at higher frequencies, the user can still hear sounds present at frequencies above 500 Hz in both the idealized bell and idealized diaphragm modes even though they have relatively greater attenuation. To eliminate contamination of the body sounds by other environmental sounds, such as low frequency hand tremor, external noise and electronic noise, the overall passband can be restricted to about 20-1000 Hz in the idealized bell and idealized diaphragm modes, and about 20-2000 Hz in the wideband mode.

As shown in embodiment 510, 530, 550, the "cross-over" frequency of the idealized bell and idealized diaphragm frequency responses can be in the range of about 100-200 Hz. A uniform, relative attenuation of 6-12 dB/octave in this range can be utilized to suppress masking of diagnostically significant sounds by other simultaneous and spectrally-adjacent sounds.

The emphasized and de-emphasized passbands in the idealized diaphragm and idealized bell modes can result in an electronic stethoscope in which the idealized bell and idealized diaphragm modes can be spectrally separate. The spectral separation of the idealized bell and diaphragm modes can allow the user to more easily hear and distinguish between different sounds of interest. The spectral separation of the emphasized frequencies with preservation of the de-emphasized frequencies of the idealized diaphragm and idealized bell modes can permit the electronic stethoscope to give the overall impression that the stethoscope preserves the sound quality of good acoustic stethoscopes, which generally are not narrow-band instruments. Reduced masking of the high or low frequency sounds provided by the idealized diaphragm and idealized bell modes, respectively, can mean better clarity for the sound of interest, leading to more effective screening and diagnosis.

The wideband mode of embodiment 510 can provide a wider sound band with similar gain across all frequencies in the passband, but with a slight (e.g., 3-5 dB) de-emphasis below 100 Hz. The wideband mode can provide a response that cannot be achieved in a traditional acoustic stethoscope, and thus can allow the user to hear sounds, such as some high frequency sounds from artificial heart valves and the like, which cannot be heard with traditional acoustic stethoscopes. For initial screening functions, auscultation can begin in the wideband mode, with the ideal bell or diaphragm mode selected as the user determines the frequency range of most interest. In addition, the wideband mode can be utilized for use with an external computer-based data acquisition (e.g., mobile phone executing specialized software) and display system (e.g., computer monitor). A data acquisition system can permit software selection of different frequency responses and the ability to display and manipulate these different responses. Audio playback and manipulation can be performed utilizing traditional and/or proprietary software algorithms. The wideband mode may be employed for this use because it passes a wider bandwidth. It shall be understood, however, that a data acquisition system, display, audio playback, etc., can be used with any of the idealized diaphragm, idealized bell, and wideband modes.

The above described operational modes can provide a user (e.g., physician) with distinctly different and advantageous sound processing modes. The idealized bell and diaphragm modes can be more spectrally separate than with traditional stethoscopes, allowing the user to more easily hear and distinguish different sounds of interest. Traditional acoustic stethoscopes typically lack a uniform relative attenuation outside of the bell/diaphragm cross-over band, due the presence of acoustic resonances. Also, the switch over between bell and diaphragm modes with traditional acoustic stethoscopes generally required gross hand movements to engage a pneumatic valve or to turn over the chestpiece. In contrast, the functionality of this disclosure can be quickly selected with the simple and easily operable power/mode switches (e.g., push button, dials). Thus, no repositioning of the chestpiece can be required to switch between bell and diaphragm modes. In addition, the wideband mode allows the user to hear a full presentation of body sounds, and can be also desirable for use with a computerized data acquisition and display system, or with an amplifier and speaker system, and the like. Finally, due to electronic filtering of the body sounds, the manufacturing process can be much more precise and repeatable than earlier non-electronic constructions.

The flowchart and block diagrams in the FIGS. 1A-5 illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A system for an electronic stethoscope comprising:
an electronic stethoscope lacking an earpiece assembly comprising of a chestpiece base, wherein the chestpiece base comprises: a diaphragm, a set of audio transducers, a computer readable storage medium, an analog-to-digital circuit, and a transceiver, wherein each of the set of transducers detects analog auscultatory sounds from an auscultatory source and converts the sounds to a digital encoding, wherein the encoding is transmitted to a proximate or remote computing device via a communication channel, wherein by lacking the earpiece assembly the electronic stethoscope does not provide a conduit for transmitting the analog auscultatory sound from the chestpiece base to the ear canal of a user, wherein the electronic stethoscope further comprises one or more feedback components for directing a user of the electronic stethoscope to adjust the position of the electronic stethoscope on a patient to improve sound quality, wherein the feedback components comprise a visual direction indication for repositioning the electronic stethoscope to improve sound quality or comprise a directional vibration that corresponds to a cardinal direction in which the electronic stethoscope is to be repositioned to improve sound quality.

2. The system of claim 1, wherein the stethoscope comprises a switch to toggle between analog and digital recording of the analog auscultatory sounds.

3. The system of claim 1, wherein the stethoscope is communicatively linked via the computing device via an encrypted communication channel, wherein the channel is at least one of a near field communication channel and a medium field communication channel, wherein the medium field communication channel is a BLUETOOTH communication channel.

4. The system of claim 1, wherein the set of transducers comprise a piezoelectric transducer.

5. The system of claim 1, further comprising:
a computer entity analyzing the digital encoding of the auscultatory sound to emulate a decision making ability of a human expert.

6. The system of claim 1, further comprising:
a computing entity analyzing the digital encoding of the auscultatory sound to determine at least one medical condition.

7. The system of claim 6, wherein the medical condition is used by an insurance entity to produce an insurance estimate for coverage of a medical service and an insurance referral for a medical service provider.

8. The system of claim 6, wherein the computing entity responsive to determinations of the at least one medical condition performing automated actions based on the at least one medical condition in response.

9. The system of claim 6, wherein the analysis by the computing entity triggers automatic insurance referrals to specialists care providers.

10. The system of claim 1, further comprising:
an application programming interface for permitting the communication of the stethoscope with a medical device.

11. A system for an electronic stethoscope comprising:
an electronic stethoscope lacking an earpiece assembly comprising of a chestpiece base, wherein the chestpiece base comprises: a diaphragm, a transducer, a computer readable storage medium, an analog-to-digital circuit, and a transceiver, wherein the transducer detects analog auscultatory sounds from an auscultatory source and converts the sounds to a digital encoding, wherein the encoding is transmitted to a proximate or remote computing device via a communication channel, wherein by lacking the earpiece assembly the electronic stethoscope does not provide a conduit for transmitting the analog auscultatory sound from the base to the ear canal of a user; and
a companion application configured to communicate with the electronic stethoscope stored within a digital storage medium of a mobile computing device, wherein the companion application performs playback of the digital encoding, wherein the companion application presents at least one medical condition determined by a computing device analyzing the digital encoding of the auscultatory sound, wherein the companion application performs at least one automated action responsive to the at least one medical condition.

12. The system of claim 11, wherein the stethoscope comprises of an audio output port permitting a wired audio headset to be physically connected to the stethoscope, wherein the wired audio headset is configured to playback in real-time the digital encoding of the auscultatory sounds.

13. The system of claim 11, wherein the electronic stethoscope further comprises one or more feedback components for directing a user of the electronic stethoscope to adjust the position of the electronic stethoscope on a patient to improve sound quality, wherein the feedback components comprise a visual direction indication for repositioning the electronic stethoscope to improve sound quality or comprise a directional vibration that corresponds to a cardinal direction in which the electronic stethoscope is to be repositioned to improve sound quality.

14. The system of claim 11, wherein an interface of the application is configured to present the encoding, wherein the encoding is able to be filtered, wherein the filters comprise of a low bandpass and a high bandpass filter.

15. The system of claim 11, wherein the application is able to compare a historic digitally encoded auscultatory recoding with the digital encoding of the auscultatory sound.

16. The system of claim 15, wherein the comparison is at least one of a visual and acoustic comparison.

17. The system of claim 11, further comprising:
the application communicatively linked to at least one of a computing device of an insurance entity and a medical facility, wherein the application is configured to convey an evaluation of the digital encoding of the auscultatory sound to the computing device.

18. A device comprising:
one or more processors; and
a non-transitory storage medium storing software application of an electronic stethoscope, wherein code of the software application is executed by the one or more processors causing the device to perform a set of actions, wherein the software application is configured to communicate with an electronic stethoscope, wherein the electronic stethoscope lacks an earpiece assembly, wherein the stethoscope comprises of a chestpiece base, an transducer, a computer readable storage medium, an analog-to-digital circuit, and a transceiver, wherein the transducer detects analog auscultatory sounds from a physiology of a user and converts the sounds to a digital encoding, wherein the encoding is wirelessly transmitted to a proximate or remote computing device via the application, wherein by lacking the earpiece assembly the electronic stethoscope does not provide a conduit for transmitting the analog auscultatory sound from the base to the ear canal of a user, wherein the device further comprises one or more feedback components for directing a user of the electronic stethoscope to adjust the position of the electronic stethoscope on a patient to improve sound quality, wherein the feedback components comprise a visual direction indication for repositioning the electronic stethoscope to improve sound quality or comprise a directional vibration that corresponds to a cardinal direction in which the electronic stethoscope is to be repositioned to improve sound quality.

19. The device claim 18, said software application further comprising:
an interface of the application configured to present the encoding, wherein the encoding is able to be filtered, wherein the filters comprise of a low bandpass and a high bandpass filter.

20. The device claim 18, wherein the software application is able to compare a historic digitally encoded auscultatory recoding with the digital encoding of the auscultatory sound, wherein the recording is a historic recording of the user.

* * * * *